(12) United States Patent
Brokx (10) Patent No.: US 8,613,618 B2
(45) Date of Patent: Dec. 24, 2013

(54) MEDICAL-DENTAL INSTRUMENTS

(75) Inventor: Petrus Johannes Wouter Brokx, Zeist (NL)

(73) Assignee: Vibringe B.V., Amsterdam (NL)

( * ) Notice: Subject to any disclaimer, the term of this patent is extended or adjusted under 35 U.S.C. 154(b) by 491 days.

(21) Appl. No.: 12/377,937

(22) PCT Filed: Feb. 20, 2008

(86) PCT No.: PCT/NL2008/000050
§ 371 (c)(1),
(2), (4) Date: Feb. 18, 2009

(87) PCT Pub. No.: WO2008/103030
PCT Pub. Date: Aug. 28, 2008

(65) Prior Publication Data
US 2010/0167234 A1    Jul. 1, 2010

(30) Foreign Application Priority Data

Feb. 21, 2007 (NL) .................................... 1033434

(51) Int. Cl.
*A61C 5/04* (2006.01)
*A61M 5/00* (2006.01)
*A61B 17/20* (2006.01)

(52) U.S. Cl.
USPC ................................ 433/90; 604/187; 604/22

(58) Field of Classification Search
USPC ............. 433/80, 81, 86, 89; 604/19, 22, 181, 604/187, 92, 82; 239/102.1–102.2
See application file for complete search history.

(56) References Cited

U.S. PATENT DOCUMENTS

| 4,463,875 | A | * | 8/1984 | Tepic | .............................. 604/87 |
| 5,080,103 | A | * | 1/1992 | Olivier | .......................... 604/117 |
| 5,423,746 | A | * | 6/1995 | Burkett et al. | .................. 604/65 |
| 6,162,202 | A |   | 12/2000 | Sicurelli et al. | |

(Continued)

FOREIGN PATENT DOCUMENTS

| DE | 19830856 A1 | 1/2000 |
| EP | 1712201 A1 | 10/2006 |

(Continued)

OTHER PUBLICATIONS

Switch. (n.d.). Dictionary.com Unabridged. Retrieved Feb. 8, 2011, from Dictionary.com website: http://dictionary.reference.com/browse/switch.*

(Continued)

*Primary Examiner* — Heidi M Eide
(74) *Attorney, Agent, or Firm* — Ryan A. Schneider, Esq.; Troutman Sanders LLP (57) ABSTRACT

A rinsing instrument (1) including a vibration part (30) and a spraying part (20) which can be coupled to each other. The spraying part includes a hollow cylindrical body (21) with an input end (23) and a narrow needle (25); an axially displaceable piston (22) arranged in the interior of the body, which at its free side directed away from the spraying mouth is provided with a coupling member (27) for coupling to the vibration part, for instance a threading. The vibration part includes a housing (31) which at an end is provided with a coupling member (32) for coupling to the spraying part, for instance a threading; a vibration generator (34) mounted in the housing, for instance a motor; a battery chamber (39) for receiving a battery (35) providing electrical supply to the vibration generator; a user-controllable switch (36) mounted in the housing for actuating the vibration generator.

14 Claims, 6 Drawing Sheets

(56) References Cited

U.S. PATENT DOCUMENTS

| | | |
|---|---|---|
| 6,602,229 B2 * | 8/2003 | Coss .............................. 604/187 |
| 6,666,875 B1 * | 12/2003 | Sakurai et al. ................. 606/169 |
| 6,723,064 B2 * | 4/2004 | Babaev ........................... 604/22 |
| 6,752,789 B2 * | 6/2004 | Duchon et al. ................ 604/228 |
| 2005/0032017 A1 * | 2/2005 | Levy ............................... 433/29 |

FOREIGN PATENT DOCUMENTS

| | | |
|---|---|---|
| EP | 1743593 A1 | 1/2007 |
| FR | 2190176 A5 | 1/1974 |
| JP | 11056879 A | 3/1999 |
| NL | 1033435 C1 | 4/2007 |

OTHER PUBLICATIONS

WO2008103030—International Preliminary Report on Patentability Chapter I (IB/373), dated Aug. 26, 2009.

WO2008103030—Written Opinion of the International Search Authority, dated Aug. 21, 2009.

* cited by examiner

MEDICAL-DENTAL INSTRUMENTS

BENEFIT CLAIMS

This application is a U.S. National Stage of International Application No. PCT/NL2008/000050, filed 20 Feb. 2008, which claims the benefit of NL 1033434, filed 21 Feb. 2007.

FIELD OF THE INVENTION

The present invention relates in general to medical-dental instruments.

BACKGROUND OF THE INVENTION

When a dentist is going to fill a molar, and particularly when he is to treat a root canal, it is usual that he rinses the cavity in the molar or root canal, respectively, for instance to remove grains and/or debris (for instance bacteria) resulting during preceding drilling actions or rasping actions. To that end, he has a kind of syringe, i.e. a piston in a cylinder, with a sharp needle of which the end is placed in the molar or root canal, respectively. The dentist presses the piston, which presses rinsing liquid out of the cylinder, and a little jet of the rinsing liquid sprays through the needle into the cavity of the root canal. The quality of the ultimate result of the treatment, for instance the filled root canal, depends among other things of a well implemented rinsing action: in case rinsing is not performed correctly and clutter or bacteria remain behind, it is possible that for instance inflammations arise.

It has appeared that the quality of the rinsing action depends to an important extent on the expertise of the dentist in question. If he generates a rinsing jet which is too powerful, for instance by using ultrasonic rinsing techniques, there is a chance on damage to the soft tooth tissue. On the other hand, a jet which is insufficiently powerful has an insufficient cleansing action.

It has appeared that, under normal circumstances, the cleansing effect of a rinsing action is often not 100%, but that the cleansing effect can be improved by vibrating the rinsing jet. This improvement of the cleansing effect is known per se, and the state of the art involves large, complicated and expensive apparatus for generating an ultrasonic vibration, which vibration is transferred to the piston/cylinder combination by means of one or more hoses. These hoses make it difficult for the rinsing syringe to be easily handled.

Furthermore, a problem of an approach according to the state of the art is that the end tip of the sharp spraying needle vibrates wildly in transverse direction, and thus can hit wildly against the wall of the root canal to be treated, which is not only unpleasant but may also lead to damaging healthy tissue.

BRIEF SUMMARY OF THE INVENTION

The present invention aims to eliminate or at least reduce the problems mentioned. More particularly, the present invention aims to provide a simplified and relatively cheap instrument, which can easily be handled and which is capable of providing an effectively vibrating rinsing jet with a good cleansing effect.

According to an important aspect of the present invention, the rinsing syringe is provided with a simple vibrating motor that is supplied by a battery. Experiments have shown that good results can be achieved in this manner.

BRIEF DESCRIPTION OF THE DRAWINGS

These and other aspects, features and advantages of the present invention will be further clarified by the following description with reference to the drawings, in which same reference numerals indicate same or similar parts, and in which.

DETAILED DESCRIPTION OF PREFERRED EMBODIMENTS

Figure 1:
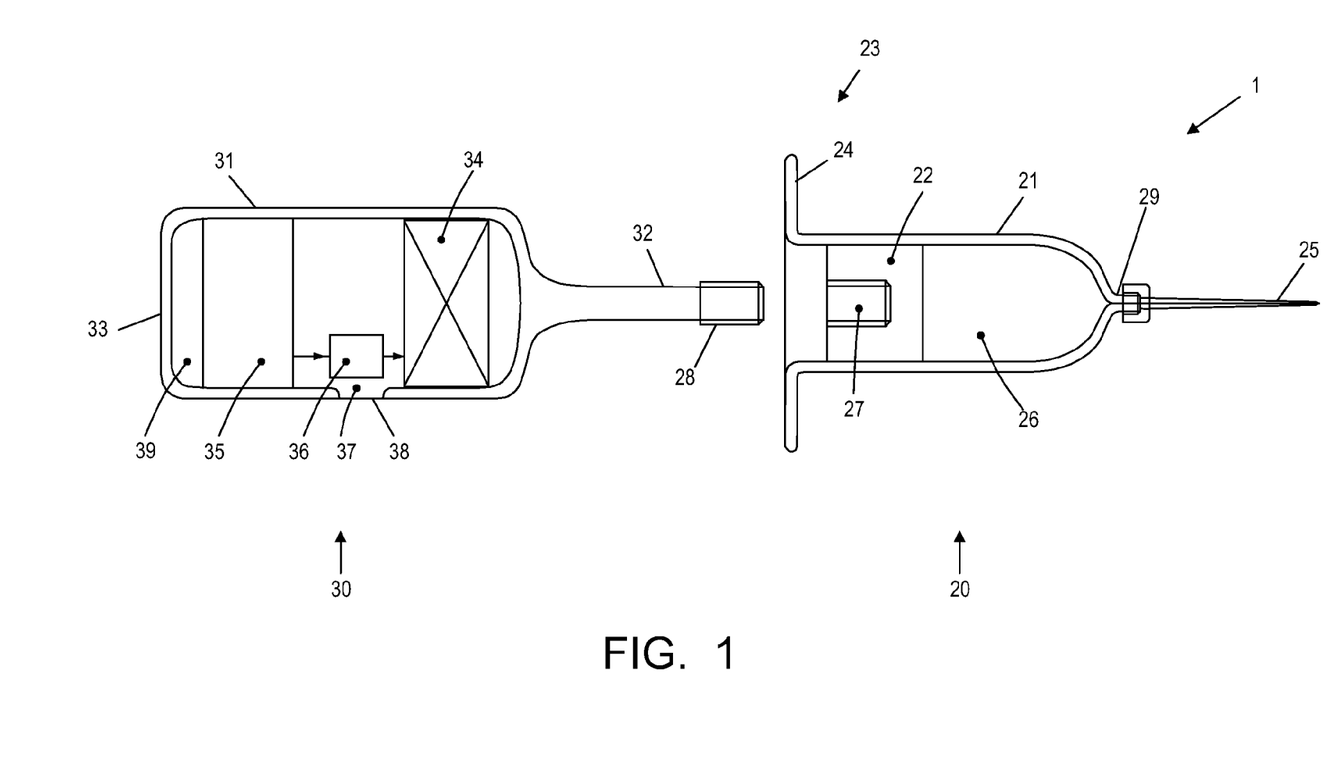
FIG. 1 schematically shows a longitudinal section of the possible embodiment of a rinsing instrument proposed by the present invention.

A rinsing instrument 1 according to the present invention is schematically shown in FIG. 1, to illustrate the operative principle thereof. The rinsing instrument 1 comprises two parts that can be coupled to each other, i.e. a spraying part 20 and a vibrating part 30.

The spraying part 20, which may be made of an at least partially transparent plastic, comprises a hollow cylindrical body 21 with an axially displaceable piston 22 arranged in the interior thereof. The cylindrical body 21, also indicated as "the cylinder", has an entry end 23 with outwardly extending wings or flange 24, typically suitable for the user (dentist) to place two fingers behind it, on opposite sides of the cylindrical body 21. At the opposite side, the cylindrical body 21 has an exit mouthpiece 29, with a spraying needle 25 attached to it, typically screwed, typically suitable for placement in a hollow root canal (and also indicated as spraying mouth or needle). The spraying mouth is only schematically shown in the drawing, since the design thereof is known per se. In more detail, it may be noted that the spraying mouth is typically implemented as a thin hollow metal needle, which is attached to the output mouthpiece 29 shortly before use. Such needles and the attachment thereof on the output mouthpiece 29, are known per se, and the usual needles and cylindrical bodies can be used when implementing the present invention. As will become clear later, the only adaptation necessary to the usual spraying parts is a coupling facility to be arranged to the piston, for coupling to a vibration generator.

Rinsing liquid 26 is located in the cylindrical body 21, between the output 25 and the piston 22. A rinsing liquid which has proven itself for this purpose is sodium hypochlorite, but other compositions are also conceivable. If a pressure force is inserted on the piston 22 in the direction of the needle 25, the piston 22 is displaced towards the needle 25, pressing rinsing liquid 26 out of the needle 25, such that a rinsing jet (not shown) flows out of the needle 25, as will be clear to the person skilled in the art.

At its free side, directed away from the needle 25, the piston 22 is provided with a coupling member 27, which in this example is implemented as a bore with internal threading. Other embodiments will also be possible, as will be clear to a person skilled in the art; by way of example, a bayonet coupling is mentioned here. A particularly favourable preferred embodiment will be discussed later.

The vibration part 30 comprises a housing 31 which at one end (in this example the right-hand end) is provided with a second coupling member 28 for coupling with the first coupling member 27 of the piston 22. In this embodiment, a stylus 32 is provided with an external threading as the second coupling member 28, which can thus be screwed into the piston 22.

The shape of the housing 31 is not critical. However, for comfort of use, the housing for instance has an elongate, cylindrical shape, with a diameter in the order of about 2-5 cm. The length preferably is in the order of about 10-15 cm. During use, the user can then place his thumb on the rear wall 33 opposite the stylus 32.

The stylus 32 is preferably substantially aligned with the body axis of the houses 31. As a result, when spraying part 20 and vibration part 30 are coupled to each other, these elongate parts are aligned with each other.

A vibration motor 34 is mounted in the housing 31. The vibration motor is a relatively small motor, with dimensions in the order of some centimetres. The vibration motor may be implemented as a motor with a weight mounted eccentrically on the output axel. In a suitable embodiment, use can be made of vibration motors such as are known for utilisation in electrical tooth brushes.

Instead of a motor (i.e. an apparatus with a rotating output axle), use can be made of a vibration generator of another type. By way of example, a vibration generator on the basis of a piezo element is mentioned here, or a vibration generator on the basis of a loudspeaker coil (linear vibration in an electrical field).

Further, a battery 35 is mounted in a battery chamber 39 of the housing 31, which provides electrical supply to the vibration generator 34. The size of the battery (and thus the type of battery) is adapted to the voltage requirements of the vibration generator 34 and to the dimensions of the housing 31. The housing 31 may be provided with a detachable lid or the like in order to be able to replace the battery 35 when empty, but this is not shown. Alternatively, it is possible that the battery 35 is a rechargeable battery, and that the housing is provided with an electrical connector for connecting an external charging apparatus, but this is also not shown. Finally, it is possible that vibration part 30 is implemented as a disposable part, that is disposed when the battery is empty.

For activating the motor 34, a switch 36 is mounted in the housing 31, that may be operated by a user. For operating the switch 36, the housing has an opening 37, with a flexible sealing member 38 mounted therein, for instance made of rubber or silicone.

The required electrical wiring in the housing 31 is not shown for sake of simplicity. Only the functional relationship between the battery 35, the switch 36 and the motor 34 is schematically shown, and therefore the switch 36 is pictured between the battery 35 and the motor 34, but it may be clear that this does not mean that the switch 36 has to be physically placed between the battery 35 and the motor 34.

Operation is as follows. The dentist has available a supply of multiple spraying parts 20, individually packed in a hermetically closed package, for sake of hygiene. When the dentist is, for instance, doing a root canal treatment and he wishes to rinse this canal, he takes a spraying part 20 out of its hermetical package and attaches the stylus 32 of the vibration part 30 to the piston 22 of the spraying part 20. Further, he applies the needle 25. In order to fill the cylinder 21, he presses the piston 22 to the back of the cylinder 21, puts the needle in a supply container with the rinsing liquid to be used, and pulls the piston 22 in the direction of the input end 23, sucking the liquid 26 through the needle 25 into the cylinder 21. He operates the switch 36 to turn on the motor 34. The motor generates a low-frequency vibration of the vibration part 30, of which the frequency may for instance be in the range of about 1 Hz to about 3000 Hz, although higher or lower frequencies are not excluded; in any case, the vibration is substantially less than ultrasonic. The vibration generated is transferred to the spraying part 20 through the stylus 32 and the coupling members 28, 27 cooperating with each other, resulting eventually in a vibration of the needle 25.

The rinsing treatment is now implemented in the usual manner. The needle 25 is placed in the root canal to be treated and the dentist presses the housing 31, causing the piston 22 to be pressed towards the needle 25 and a jet of rinsing liquid to exit the needle 25. Because of the vibration generated in the spraying part 20 and the needle 25, also the jet of rinsing liquid will vibrate, resulting in the desired improved cleansing effect.

If desired, the above is repeated one or more times.

After performing the rinsing action, the dentist may turn off the motor 34 again and disconnect the spraying part 20 from the vibration part 30. The spraying part 20 including the needle 25 may be disposed, the vibration part 30 may be used for multiple rinsing treatments.

Figure 2:
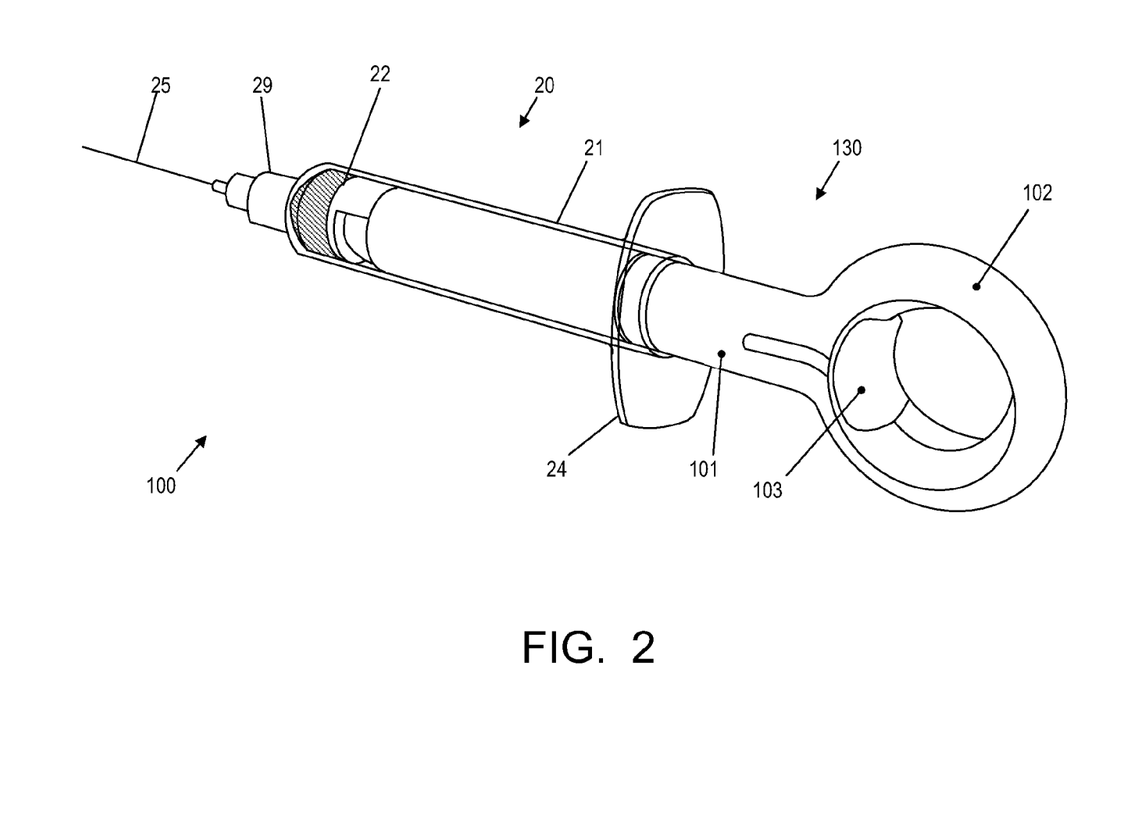
FIG. 2 schematically shows a perspective view of a preferred embodiment of a rinsing instrument according to the present invention.

FIG. 2 schematically shows a perspective view of a preferred embodiment of the rinsing instrument, generally indicated with the reference numeral 100. In this preferred embodiment, the vibration part, indicated by reference numeral 130, is implemented as an elongate cylindrical house part 101 with at its rear side a ring part 102 formed to it, suitable for a dentist to put his thumb through it. At the front side of the ring 102, where the ring 102 attaches to the housing part 101, the ring 102 is at its inner side provided with a pressure switch 103, controlling the motor (not shown). Hereby, the important advantages are combined that the dentist has a good grip on the rinsing instrument, and that the motor is automatically actuated when the dentist exerts sufficient pressure on the vibration part 130, and thus to the pressure switch 103, to press the piston 22 towards the needle 25.

Preferably, a rechargeable battery is incorporated in the vibration part 130. In principle, it is possible that an "ordinary" battery is used, but it is considered to be a disadvantage that it is then necessary to regularly open the vibration part 130 to replace the battery. Also in the case of a rechargeable battery one may chose to exchange this battery when empty, but preferably use is made of a remote charging. To this end, the vibration part 130 is preferably provided with a reception coil for electromagnetic energy, and the ring 102 offers the advantage that it is perfectly suitable to accommodate the reception coil. Since remote charging of rechargeable batteries by means of a transmission coil and reception coil is known per se, this does not have to be explained any further.

Figure 3:
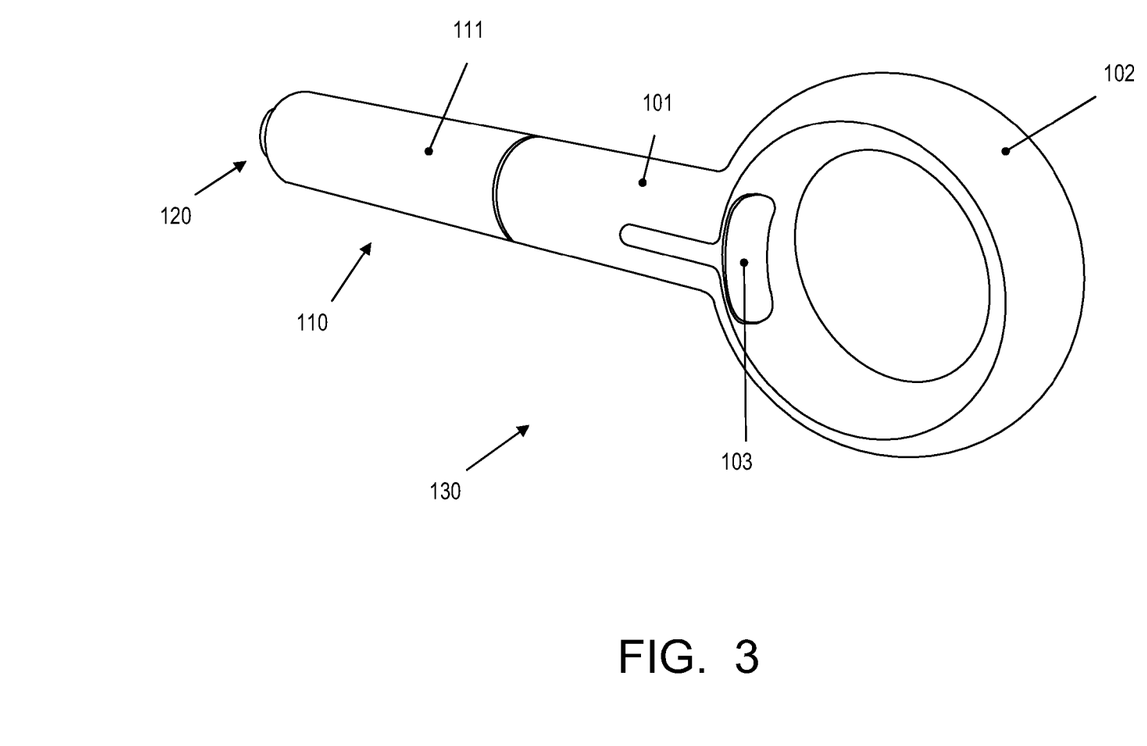
FIG. 3 is a schematic perspective view of a vibrating part.

FIG. 3 is a perspective view of the vibration part 130, removed from the cylinder 21. Around the front part 110 of the cylindrical house part 101, that is pressed into the cylinder 21 during use, a metal sleeve 111 is preferably arranged, for protection. At the free front end of cylindrical house part 101, a coupling member 120 is arranged, which will be described later.

Figure 4A:
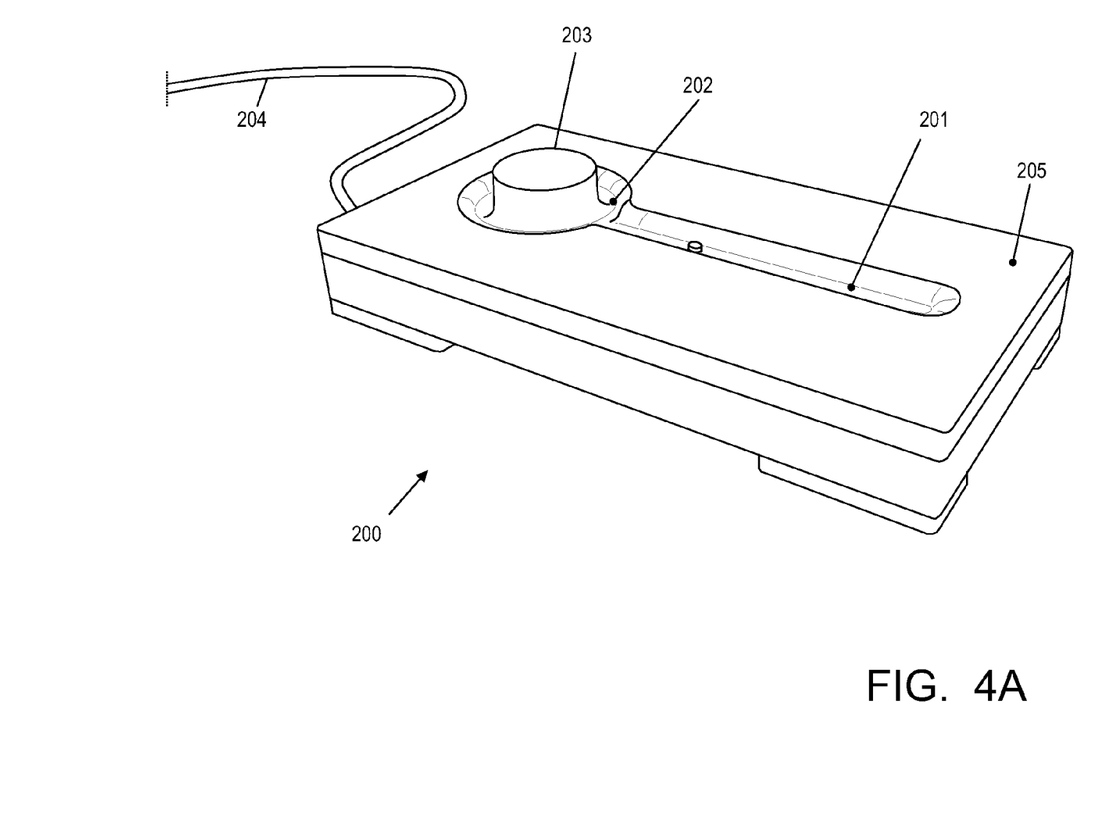
FIGS. 4A and 4B illustrate a docking station.
Figure 4B:
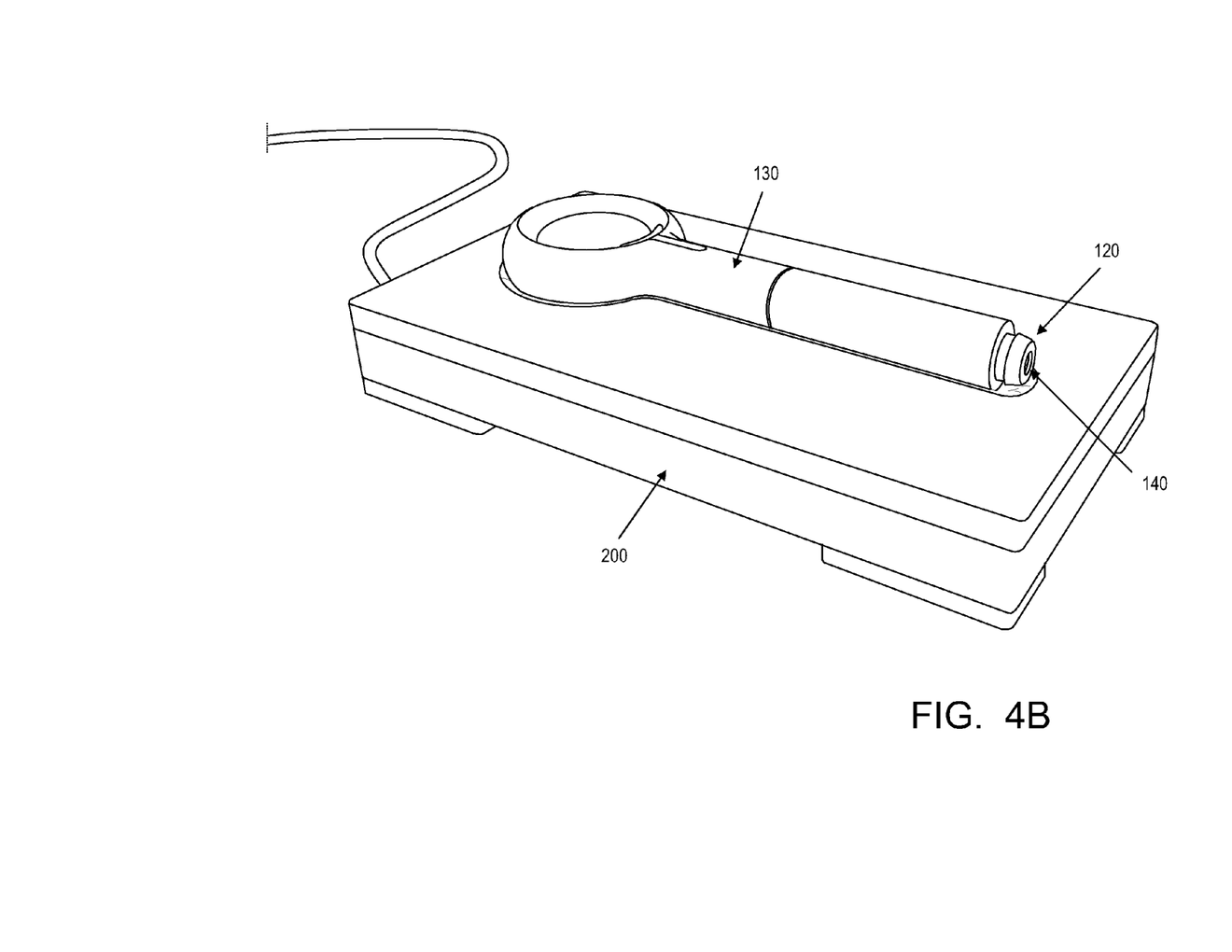

For charging the rechargeable battery in the vibration part 130, the present invention proposes a docking station 200, of which FIG. 4A shows a schematic perspective view. FIG. 4B shows a comparable perspective view, now with the vibration part 130 applied. In this embodiment, the docking station 200 in general has a rectangular shape, with an upper surface 205, in which an elongate recess 201 is formed for accommodating the cylindrical house part 101. At one end, the elongate recess 201 connects to a circular recess 202 for accommodating the ring 102. Centrally within the circular recess 202, the docking station 200 has a mesa 203 extending above the upper surface 205, in which mesa a transmission coil (not shown) for the electromagnetic energy transfer is located. A connection for the electronics within the docking station 200 is shown at 204. Because of the design of the mesa 203 extending within the ring 102, in which the transmission coil is arranged, a good electromagnetic coupling is achieved.

Figure 5:
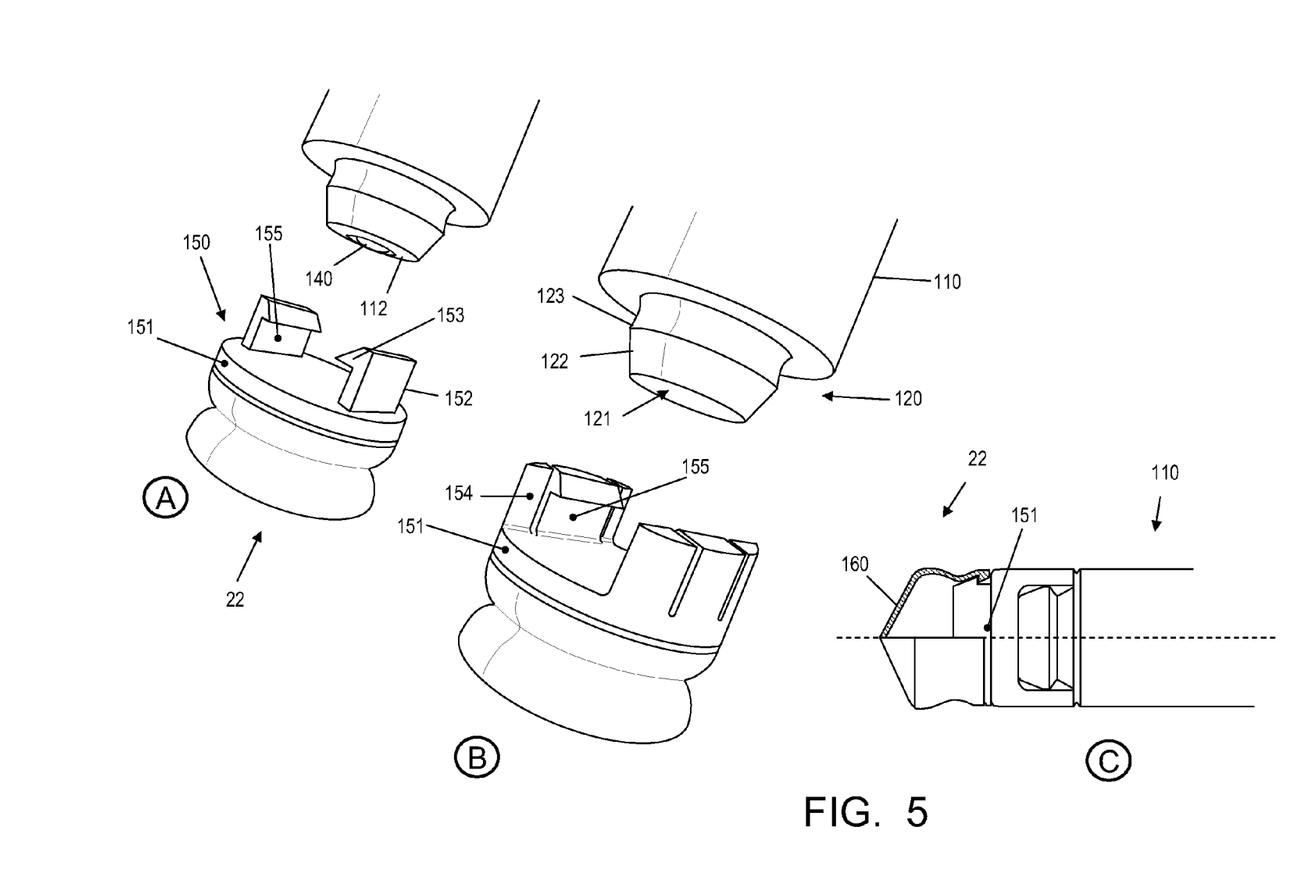
FIG. 5 is a schematic perspective view showing details of the coupling between a piston and a vibrating part.

FIG. 5 is a schematic perspective view showing details of a preferred design for the coupling between the front part 110 of the cylindrical house part 101 of the vibration part 130 and the piston 22 in the cylinder 21. In this preferred design, the piston 22 at its rear side (directed away from the needle 25) is provided with coupling members 150 comprising a disk-shaped carrier 151 with gripping arms 152 arranged along the circumference thereof, opposite each other, and directed substantially parallel to the longitudinal axes of the cylinder 21, the gripping arms 152 at their ends being provided with inwardly extending, barb-shaped or arrow-shaped projections 153. The number of gripping arms 152 in the figure at the variations A and B is shown as being equal to 2, but this number may also be higher. The gripping arms may stand freely (variation A) or may be flanked by support members 154 (variation B). For cooperation with these coupling members 150, a coupling member 120 arranged at the end of the cylindrical house part 101 preferably has the shape of an axial stylus 121 with a oblique run-in face 122 and a gripping edge 123, behind which the barb-shaped or arrow-shaped extensions 153 of the gripping arms 152 can engage.

An advantage of this design is that it is a relatively simple and cheap design, which makes it possible that the vibration part 130 is coupled to the piston 22 by an axially directed pressure force (see detail C, where the cylinder 21 is left away for sake of simplicity). During use, the piston 22 is held firmly in and by the cylinder 21; it can not come loose by vibration. After use, the vibration part 130 with the piston 22 is pulled out of the cylinder 21. In the embodiment with two gripping arms 152 standing opposite each other, wherein the inner surfaces 155 directed towards each other of these gripping arms 152 are mutually parallel surfaces, the piston 22 then can be simply disconnected from the coupling member 120 of the vibration parts 130 by a shifting displacement parallel to these inner surfaces 155, thus perpendicular to the plane of drawing in detail C.

It is noted that piston 22 comprises a fitting 160 extending over the front face of the piston, for instance made of rubber or silicone or another suitable material, that is in contact with the rinsing liquid and effects a liquid sealing with respect to the cylinder 21. This fitting 160 is attached to the disk shaped carrier 151, as illustrated in detail C.

In a preferred embodiment, an illumination element, typically an LED, is arranged in the front part 110 of the cylindrical house part 101 of the vibration part 130. This LED may be supplied from the same battery which supplies the motor, and may be switched ON/OFF simultaneously with the motor or via a separate switch (not shown). The illumination element may be arranged at any position in the front part 110 of the cylindrical house part 101, but advantageously the LED is located at the end face 112 of the front part 110 of the cylindrical house part 101, as shown in FIG. 4B and in FIG. 5 at detail A. To this end, a bore can be arranged in this end face 112, in which the LED fits; if desired, a transparent cover plate (not shown) may be arranged over the LED.

The illumination element 140 offers the dentist additional light in the mouth of the patient, so that he can well see where he places the needle 25. Further, the illumination element 140 offers an illumination of the liquid level in the (transparent) cylinder 21, so that the dentist can well see how far he has pressed the piston 22 into the cylinder 21. It is advantageous if the body of the piston 22, particularly the disk shaped carrier 151 and the fitting 160, are made of a transparent material.

It will be clear to a person skilled in the art that the invention is not limited to the exemplary embodiments discussed in the above, but that several variations and modifications are possible within the protective scope of the invention as defined in the attached claims.

For instance, it is possible that a vibrating liquid jet is used for another reason than rinsing a root canal. It is also possible that the instrument with the vibrating needle is intended to be used for doing injections.

What is claimed is:

1. Vibration part of an instrument, the instrument including a spraying part for spraying liquid, the vibration part of the instrument providing vibration to the spraying part to impart a vibration to the sprayed liquid, the spraying part of the instrument comprising a hollow cylindrical body with an input end and an output mouth piece for attaching a spraying needle there on, the spraying part of the instrument further comprising an axially displaceable piston arranged in the interior of the hollow cylindrical body, the displaceable piston having a free side directed away from the output mouthpiece, the free side of the displaceable piston having a piston coupling member, the vibration part of the instrument comprising:
   a coupling member for coupling to the piston coupling member of the spraying part, wherein the coupling member axially displaces the piston of the spraying part through the hollow cylindrical body;
   a vibration generator mounted in a housing;
   a battery chamber for receiving a battery that provides electrical supply to the vibration generator; and
   a switch mounted in the housing, operable by a user for actuating the vibration generator;
   wherein the vibration part imparts a vibration generated by the vibration generator to the spraying part of the instrument through the coupling member, resulting in a vibration of the output mouth piece of the spraying part; and
   wherein the sprayed liquid exits the instrument through the axial displacement of the piston and the vibration imparted on the sprayed liquid is transferred through the coupling member of the vibration part.

2. Vibration part according to claim 1, wherein the coupling member is fittable within the piston coupling member of the displaceable piston of the spraying part.

3. Vibration part according to claim 1, wherein the vibration generator comprises a vibration motor.

4. Vibration part according to claim 1, further comprising one or more of the following features a] to h]:
   a] the coupling member is provided with a threading;
   b] the vibration generator comprises a piezo element;
   c] the vibration generator comprises a loudspeaker coil;
   d] the housing is implemented as a disposable part that is disposed when the battery is empty;
   e] the housing comprises the coupling member for detachably coupling to the piston coupling member, and the housing has an elongate, cylindrical shape;
   f] the housing comprises the coupling member for detachably coupling to the piston coupling member, and the housing has a diameter in the order of about 1-5 cm;
   g] the housing comprises the coupling member for detachably coupling to the piston coupling member, and the housing has a length in the order of about 10-15 cm;
   h] the housing, at the location of the switch, has an opening with a flexible sealing member mounted therein, in order to allow actuation of the switch.

5. Vibration part according to claim 1, wherein:
   the housing comprises the coupling member for detachably coupling to the piston coupling member, and the housing is an elongate cylindrical house part fitting in the hollow cylindrical body, the cylindrical house part having a ring part formed at its rear side, wherein the house part at its end directed away from the ring part is provided with the coupling member for coupling with the piston; and wherein the switch is located at the inner front side of the ring.

6. Vibration part according to claim 5, wherein the vibration generator comprises a vibrator motor.

7. Vibration part according to claim 6, wherein the vibrator motor has an eccentric weight on an output axle.

8. Vibration part according to claim 5, further comprising an electrical charging circuit for charging a rechargeable battery incorporated in the house part, the charging circuit comprises a reception coil for wirelessly receiving electromagnetic energy, wherein the reception coil is accommodated in the ring.

9. Vibration part according to claim 5, wherein the coupling member of the vibration part has the shape of an axial stylus with an oblique run-in face and a gripping edge; and wherein barb-shaped or arrow-shaped extensions of the piston coupling members can engage behind the gripping edge.

10. Vibration part according to claim 5, wherein an illumination element is accommodated in the cylindrical house part.

11. Vibration part according to claim 10, wherein the illumination element is accommodated in the cylindrical house part at an end face of the cylindrical house part.

12. Vibration part according to claim 1, wherein the vibration part axially displaces the piston of the spraying part through the hollow cylindrical body via an exerted pushing force or pulling force on the piston.

13. Vibration part according to claim 1, wherein the vibration part itself is axially displaceable through the hollow cylindrical body.

14. Vibration part according to claim 1, wherein the coupling member of the vibration part is fixedly coupled to the piston coupling member of the spraying part.

* * * * *